(12) United States Patent  (10) Patent No.: US 12,324,907 B2
He  (45) Date of Patent: Jun. 10, 2025

(54) ELECTRODE PLATE AND WEARABLE DEFIBRILLATION DEVICE

(71) Applicant: MICROPORT SOARING CRM (SHANGHAI) CO., LTD., Shanghai (CN)

(72) Inventor: Mingchen He, Shanghai (CN)

(73) Assignee: MICROPORT SOARING CRM (SHANGHAI) CO., LTD., Shanghai (CN)

( * ) Notice: Subject to any disclaimer, the term of this patent is extended or adjusted under 35 U.S.C. 154(b) by 370 days.

(21) Appl. No.: 17/928,139

(22) PCT Filed: Apr. 30, 2021

(86) PCT No.: PCT/CN2021/091765
§ 371 (c)(1),
(2) Date: Nov. 28, 2022

(87) PCT Pub. No.: WO2021/238593
PCT Pub. Date: Dec. 2, 2021

(65) Prior Publication Data
US 2023/0211150 A1  Jul. 6, 2023

(30) Foreign Application Priority Data
May 29, 2020 (CN) .......................... 202010479606.3

(51) Int. Cl.
*A61N 1/39* (2006.01)
*A61N 1/04* (2006.01)

(52) U.S. Cl.
CPC ........... *A61N 1/046* (2013.01); *A61N 1/0484* (2013.01); *A61N 1/3904* (2017.08)

(58) Field of Classification Search
CPC ..... A61N 1/046; A61N 1/3904; A61N 1/3968
See application file for complete search history.

(56) References Cited

U.S. PATENT DOCUMENTS 4,928,690 A * 5/1990 Heilman .............. A61B 5/6831
  600/509
5,078,134 A * 1/1992 Heilman ................ A61N 1/046
  607/142
(Continued)

FOREIGN PATENT DOCUMENTS

CN  106999708 A  8/2017
CN  206365888 U  8/2017
(Continued)

*Primary Examiner* — Eric D. Bertram
(74) *Attorney, Agent, or Firm* — Muncy, Geissler, Olds & Lowe, P.C.

(57) ABSTRACT

An electrode plate (100) and a wearable defibrillation device are disclosed. The electrode plate (100) includes a hermetic shell (110), a capsule (120) and a sealing structure (130). The hermetic shell (110) has an inflation port (111) and an overflow aperture (112). The overflow aperture (112) is disposed in a conductive exposed surface (113) of the hermetic shell (110). The capsule (120) is provided in the hermetic shell (110) and defines a cavity (122) for storage of a conductive paste therein. The cavity (122) defines an inlet orifice (123) and an outlet orifice (124). The overflow aperture (112) is disposed at the outlet orifice (124). A sealing component (132) of the sealing structure (130) is positioned at the overflow aperture (112) and configured to close the overflow aperture (112) and the outlet orifice (124) when the hermetic shell (110) is not inflated. The force applying component (131) of the sealing structure (130) is disposed on the hermetic shell (110) and then is connected to the sealing component (132) after being inserted into the capsule (120) through the inlet orifice (123). The force applying component (131) is configured to pull the sealing component (132) as a result of inflation and expansion of the hermetic shell (110) and thus open the overflow aperture (112) and the outlet orifice (124) and bring them into communication. As a result, the conductive paste is allowed (Continued)

to flow through the outlet orifice (124) and the overflow aperture (112) onto the exposed surface (113). During cardiac defibrillation of the electrode plate (100), the conductive paste can automatically applied to provide a patient with timely protection, and the conductive paste can be released in a reliable and safe manner.

15 Claims, 12 Drawing Sheets

(56) References Cited

U.S. PATENT DOCUMENTS

| | | | |
|---|---|---|---|
| 2014/0207201 A1* | 7/2014 | Piha | A61N 1/3918 |
| | | | 607/142 |
| 2016/0375262 A1 | 12/2016 | Meeker | |
| 2018/0036546 A1* | 2/2018 | Gross | A61B 5/361 |
| 2018/0272147 A1* | 9/2018 | Freeman | G16H 50/30 |
| 2019/0232071 A1* | 8/2019 | Hulings | A61N 1/3968 |
| 2019/0240497 A1* | 8/2019 | Meeker | A61N 1/0492 |
| 2022/0184406 A1* | 6/2022 | Lycke | A61N 1/3904 |
| 2023/0201570 A1* | 6/2023 | He | A61B 5/256 |
| | | | 607/5 |

FOREIGN PATENT DOCUMENTS

| | | |
|---|---|---|
| CN | 108290035 A | 7/2018 |
| CN | 109718472 A | 5/2019 |
| WO | WO2016149450 A1 | 9/2016 |

* cited by examiner

ELECTRODE PLATE AND WEARABLE DEFIBRILLATION DEVICE

TECHNICAL FIELD

The present invention relates to the field of medical devices and, in particular, to an electrode plate and a wearable defibrillation device.

BACKGROUND

In life, cardiac ventricular fibrillation is a commonly seen heart disease, it is characterized by no sign of onset, a short rescue time (only 4 minutes from the onset to death) and a high sudden death rate. For patients with this disease, the current emergency treatment approach is mainly to defibrillate the heart by delivering a high DC voltage to the heart, restoring the heart to a normal rhythm. Existing defibrillator devices can be categorized primarily into the following four types:
 (1) mobile defibrillators, which can be moved but are inconvenient to carry due to bulkiness and therefore mostly deployed in hospitals;
 (2) automated external defibrillators (AED), which are easy to carry and usually placed at highly noticeable locations in public places;
 (3) implantable cardioverter-defibrillators (ICD), which are operable in a fully automated manner and can be implanted into patients; and
 (4) wearable cardioverter-defibrillators (WCD), which are operable in a fully automated manner and used principally for patient protection from diagnosis to ICD implantation and on patients unsuitable for ICD implantation.

The former two types of defibrillator devices require manual operation. However, a patient usually loses consciousness within ten to twenty seconds after onset, and such a short period of time would present extreme challenges to manual operation. Therefore, these devices are not suitable for constant patient protection. By contrast, the latter two types of defibrillator devices are both operable in a fully automated manner not requiring manual operation and thus suitable for constant patient protection. At present, WCD devices have been widely used in clinical practice because they do not require surgical implantation and can be easily removed.

FIG. 1 explains how a conventional wearable cardioverter-defibrillator (WCD) device is used. As shown in FIG. 1, the WCD device is meant to be worn on the upper torso in the form of a shoulder strap harness and includes a shoulder strap 1, a defibrillation pad 2, a sensing electrode 3, a host 4 and an airbag 5. The specific operating principle is that the sensing electrode 3 senses an ECG signal and feeds the ECG signal to the host 4. The host 4 responsively produces an electrocardiogram and makes a determination based on the electrocardiogram. If it is determined that the patient is experiencing ventricular fibrillation, then the airbag 5 on the shoulder strap 1 is inflated to compress the defibrillation pad 2 against the patient's skin, and the defibrillation pad 2 is caused to deliver a high DC voltage for defibrillation treatment. One challenge with this defibrillator device is that, before the electric defibrillation by the electrode plate, the contact resistance between the defibrillation pad 2 and the skin must be small enough, otherwise a relatively large contact resistance would tend to burn the patient's skin and myocardium when the electric defibrillation by the defibrillation pad, or even fail defibrillation for emergency protection of the patient.

In order to tackle this challenge, a capsule containing a conductive paste is burst under the action of a large amount of gas produced by an ignited gas-producing pellet, so that the defibrillation pad is coated, thereby reducing impedance between the conductive surface of the therapy electrode and the patient's skin. However, this approach is disadvantageous in that, in order to create a gas pressure by explosion of the gas-producing agent, which is sufficiently high to cause the gas to break open the capsule, a box for enclosing the capsule must be designed to be as strong as possible. As a result, the box has to have sufficiently thick and hard walls, which would cause discomfort to a patient who is wearing the device and make him/her not willing to put it on anymore. Moreover, it is difficult to guarantee the safety of the gas-producing agent. Further, in case multiple capsules are used, if there are strength differences between them, individual capsules may be broken open. As the broken ones will cause gas leakage and hence an abrupt pressure drop, the others cannot be broken any more and the conductive paste contained therein cannot be released. As a consistent amount of released conductive paste cannot be guaranteed, it is impossible to ensure that the defibrillator device can always function in a timely way to provide the patient with emergency protection. Thus, the approach suffers from insufficient reliability.

SUMMARY OF THE INVENTION

In order to overcome the above-described problems, it is an object of the present invention to provide an electrode plate and a wearable defibrillation device, which enables automatic coating of a conductive paste and can protect a patient in a timely manner. Moreover, the conductive paste is released in a reliable and safe manner. In particular, the electrode plate can be made lightweight and slim enough to increase the patient's wearing comfort and compliance.

To this end, in one aspect of the present invention, there is provided an electrode plate for use in cardiac defibrillation, which includes:
 a hermetic shell having an inflation port and an overflow aperture, the overflow aperture provided in an exposed surface of the hermetic shell, which is conductive;
 a capsule disposed within the hermetic shell, the capsule defining a cavity for storage of a conductive paste therein, the cavity defining an inlet orifice and an outlet orifice, the overflow aperture disposed at the outlet orifice, the cavity isolated from a hollow internal space of the hermetic shell; and
 a sealing structure including a sealing component and a force applying component, the sealing component disposed at the overflow aperture, the sealing component configured to close the overflow aperture and the outlet orifice when the hermetic shell is not inflated, the force applying component disposed on the hermetic shell and coupled to the sealing component after being inserted into the capsule through the inlet orifice, the force applying component configured to pull the sealing component as a result of inflation and expansion of the hermetic shell and thus open the overflow aperture and the outlet orifice and bring them into communication.

Optionally, part of the force applying component may be disposed out of the hermetic shell, with the rest thereof being inserted into the capsule through the inlet orifice and threadedly coupled to the sealing component.

Optionally, the overflow aperture may be an internally threaded bore, with the sealing component being inserted into the internally threaded bore and threadedly coupled to the hermetic shell in a sealing manner.

Optionally, an inner wall of the hermetic shell may be provided with a threaded boss providing the internally threaded bore, wherein the threaded boss extends through the outlet orifice into the interior of the capsule, and wherein the capsule is coupled to the threaded boss in a sealing manner.

Optionally, the sealing component may include a barrier sheet and a connecting member provided on the barrier sheet, the barrier sheet provided on the hermetic shell so as to cover the overflow aperture, wherein the rest of the force applying component is inserted through the inlet orifice into the interior of the capsule and coupled to the connecting member.

Optionally, the connecting member may be a threaded boss extending through the outlet orifice into the interior of the capsule and defining a blind threaded bore, wherein the rest of the force applying component is inserted through the inlet orifice into the interior of the capsule and threadedly coupled to the threaded boss in a sealing manner.

Optionally, the hermetic shell may include a defibrillation panel and a rear shell member, which are coupled together to form an enclosed casing, the defibrillation panel providing the exposed surface, the defibrillation panel having material strength that is higher than material strength of the rear shell member, the rear shell member configured to be deformable as a result of filling a gas into the hermetic shell through the inflation port.

Optionally, the defibrillation panel may include a conductive panel and a front shell member, wherein both the front shell member and the rear shell member are insulators, and the conductive panel is a conductor, wherein the front shell member and the rear shell member are coupled together to form the enclosed casing, wherein the conductive panel provides the exposed surface and is disposed on the side of the front shell member away from the rear shell member, wherein the capsule is disposed within the enclosed casing and is disposed on the front shell member, and wherein material strength of the front shell member is higher than the material strength of the rear shell member.

Optionally, the overflow aperture may be disposed in the front shell member, with the sealing component being disposed on the conductive panel so as to cover the overflow aperture.

Optionally, the defibrillation panel may be made of conductive rubber. Alternatively, it may be a composite structure made of insulating rubber and a metallic material, or of a metallic material and plastic.

Optionally, the barrier sheet and the hermetic shell may be formed integrally with each other, with a weakened feature being provided on the barrier sheet. The weakened feature may be able to withstand a maximum pressure lower than a maximum pressure that the rest of the hermetic shell is able to withstand.

Optionally, the weakened feature may be a groove.

Optionally, the barrier sheet and the conductive panel may be formed integrally with each other, with the overflow aperture being provided in the front shell member.

Optionally, an inner surface of the rear shell member may be provided thereon with a bump protruding toward the defibrillation panel and/or annular corrugations.

Optionally, the electrode plate may further include a securing plate provided on the side of the rear shell member away from the defibrillation panel, wherein the rear shell member is coupled to the defibrillation panel via the securing plate by screws.

Optionally, the electrode plate may further include a reinforcing plate, which is disposed on the side of the rear shell member away from the defibrillation panel and coupled to the rear shell member.

Optionally, a capsule receptacle may be provided within the hermetic shell, and the capsule may be secured in the capsule receptacle.

Optionally, the inner surface of the rear shell member may be provided thereon with a protrusion configured for abutment of the capsule thereagainst.

Optionally, the protrusion may be a flat gasket glued to the rear shell member.

Optionally, the hermetic shell may further include a cable port and a terminal post, the cable port configured for passage of an external lead cable therethrough into the hermetic shell and connection with the terminal post, the terminal post electrically connected to the exposed surface.

Optionally, the capsule may include a body that defines the cavity and a collar extending outward from the body, the collar defining a hollow channel acting as the outlet orifice, the collar provided with a footing support which extends outward, extends around an axis of the collar and is provided on an inner wall of the hermetic shell.

Optionally, the capsule may be provided with annular corrugations.

Optionally, a plurality of the capsules may be included.

Optionally, the hermetic shell further includes an injection port, through which the conductive paste can be injected into the capsule.

In another aspect of the present invention, there is provided a wearable defibrillation device, which includes a vest and, provided on the vest, a sensing electrode, a host, an airbag and the electrode plate as defined in any of the preceding paragraphs.

Optionally, the electrode plate may be configured as the airbag.

In the electrode plate and wearable defibrillation device of the present invention, the force applying component pulls the sealing component off the overflow aperture and thus separates it from the sealing component, under the action of expansion of the hermetic shell, thereby opening the overflow aperture and the outlet orifice of the capsule. In this way, automated application of the conductive paste is achieved, facilitating timely protection of a patient. Compared with breaking the capsule under the action of a sufficiently high gas pressure brutally created by explosion of a gas-producing agent, according to the present invention, by introducing a gas into the electrode plate through the inflation port, it can be ensured that the force applying component pulls the sealing component to cause its complete or partial separation from the overflow aperture under the effect of a relatively safe inflation pressure. Therefore, the electrode plate and wearable defibrillation device of the present invention provides particularly high safety and reliability. Further, the hermetic shell of the present invention can expands by inflating it at a relatively low inflation pressure. This allows the hermetic shell to be designed sufficiently lightweight and slim to provide increased wearing comfort and compliance. Furthermore, the electrode plate of the present invention is an inexpensive disposable product, which can relieve the patient's treatment burden.

The hermetic shell of the electrode plate of the present invention includes a defibrillation panel and a rear shell member, the material strength of the defibrillation panel is higher than that of the rear shell member. With this arrangement, on the one hand, the electrode plate is overall soft and can provide good wearing comfort, and on the other hand, it still exhibits sufficient toughness, which prevents defibrillation performance degradations of the electrode plate when it is twisted and deformed during the patient's daily wearing, for example, during his/her physical activities.

In order to enable the sealing component to be pulled to open the overflow aperture and the outlet orifice and thus bring them into communication with each other, in the electrode plate of the present invention, the overflow aperture may be configured as an internally threaded bore, which allows the overflow aperture to be occluded and closed simply by locking the sealing component therein. Moreover, simply by tightening the force applying component and the sealing component against each other, the force applying component is able to pull the sealing component and thereby cause its complete or partial separation from the overflow aperture as a result of inflating the hermetic shell to cause its expansion. Alternatively, the barrier sheet may be provided to cover the overflow aperture, and the overflow aperture and the outlet orifice may be opened and brought into communication with each other, simply by causing the force applying component to pull the connecting member on the barrier sheet. These configurations are simple in structure and easy to achieve while providing high safety and reliability.

In the electrode plate of the present invention, the rear shell member of the hermetic shell is provided on an inner surface thereof with a bump protruding toward the defibrillation panel, and/or the rear shell member is provided on an inner surface thereof with annular corrugations. Both bump and annular corrugations can increase the amount of deformation of the hermetic shell, which imparts controllability to the process of pulling the hermetic shell to open the overflow aperture and allows for more reliable and convenient release of the conductive paste.

In the electrode plate of the present invention, the protrusion provided on the inner surface of the rear shell member can compress and hold the capsule to prevent it from falling off during daily wearing. In order to more firmly secure the capsule, the capsule receptacle may be provided in the hermetic shell.

In the electrode plate of the present invention, a plurality of the capsules are preferably included to achieve an increased amount of released conductive paste, a larger coated area and higher defibrillation safety. In particular, during release of the conductive paste, as the cavities of the capsules are all isolated from the hollow internal space of the hermetic shell, even when any overflow aperture is opened, no press drop that may make the remaining capsules impossible to be opened anymore will occur within the hermetic shell, ensuring reliable release of the conductive paste.

The electrode plate of the present invention can directly function as the airbag. In this way, the use of a separate airbag is dispensed with, and the electrode plate can be compressed against the patient's skin and the conductive paste can be released, simply by inflating the electrode plate. This makes the defibrillation device simpler in structure and easier to operate.

BRIEF DESCRIPTION OF THE DRAWINGS

The accompanying drawings are provided to facilitate a better understanding of the present invention and do not unduly limit the scope thereof in any sense. In these figures.

DESCRIPTION OF REFERENCE NUMERALS IN DRAWINGS

Figure 1:
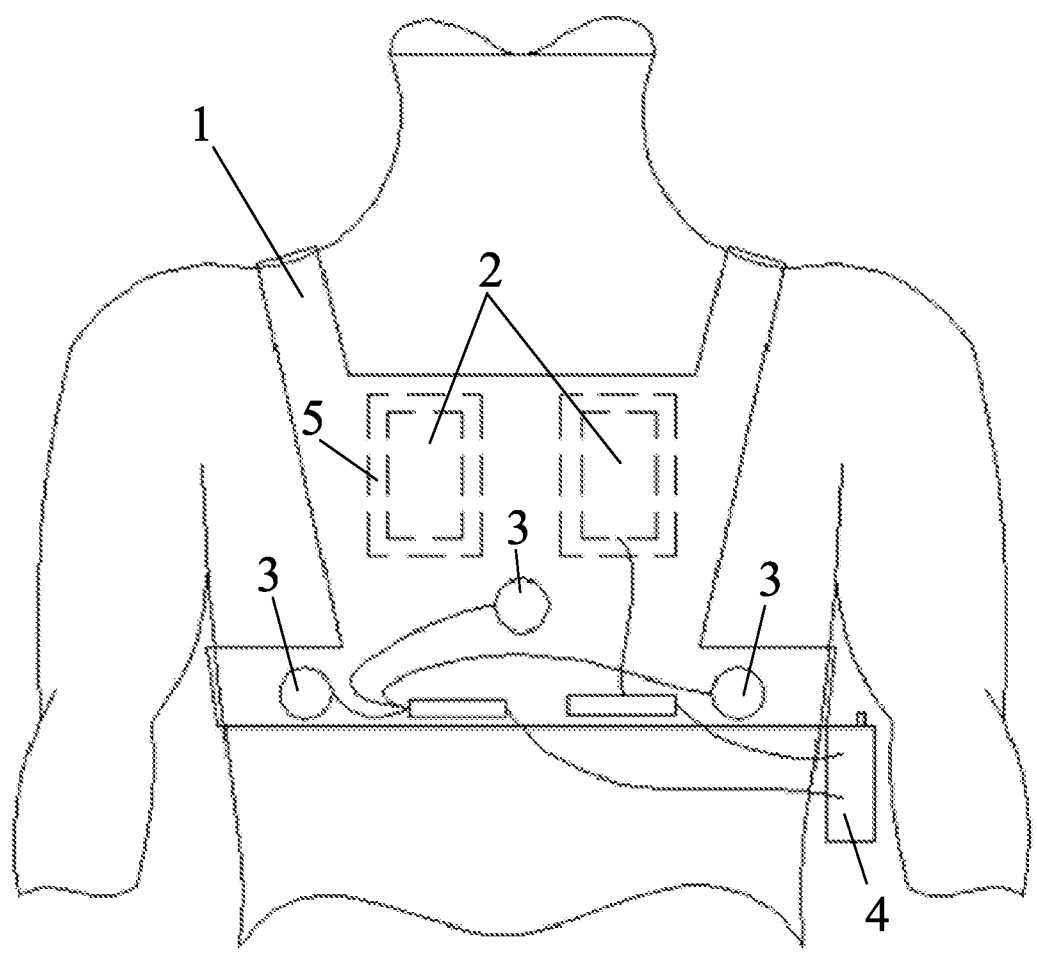
FIG. 1 explains how a conventional wearable cardioverter-defibrillator is used.

1—Shoulder Strap; 2—Electrode plate; 3—Sensing Electrode; 4—Host; 5—Airbag;
100, 600—Electrode plate; 110, 610—Hermetic Shell; 111—Inflation Port; 112, 612—Overflow Aperture; 113—Exposed Surface; 114—Mounting Hole; 115—Threaded Boss; 116—Cable Port; 117—Screw Receptacle;
110a, 610a—Defibrillation Panel; 110b, 610b—Rear Shell Member; 610c—Conductive Panel; 610d—Front Shell Member; 613—Terminal Post; 614—Capsule Receptacle; 615—Bump;

120, 620—Capsule; 121—Body; 122—Cavity; 123—Inlet Orifice; 124—Outlet Orifice; 125—Collar; 126—Footing Support;
130, 630—Sealing Structure; 131, 631—Fastening Screw; 132—Sealing Screw; 632—Barrier Sheet; 633—Threaded Boss;
640—Securing Plate; 650—Reinforcing Plate; 660—Flat Gasket;
S—Conductive Paste; 200—Vest; 300—Sensing Electrode; 400—Host; 500—Airbag.

DETAILED DESCRIPTION

Embodiments of the present invention will be described below by way of particular examples. Based on the disclosure and teachings provided herein, a person of ordinary skill in the art will readily realize other advantages and benefits provided by the present invention. The present invention may also be otherwise embodied or applied through different embodiments, and various modifications or changes may be made to the details disclosed herein from different points of view or for different applications, without departing from the spirit of the present invention. It should be noted that the accompanying drawings are provided herein merely to schematically illustrate the basic concept of the present invention. Accordingly, they only show components relating to the present invention but not necessarily depict all the components as well as their real shapes and dimensions in practical implementations. In practice, the configurations, counts and relative scales of the components may vary arbitrarily and their arrangements may be more complicated.

In the following, each of the embodiments is described as having one or more technical features. However, this does not mean that the present invention must be practiced necessarily with all such technical features, or separately with some or all the technical features in any of the embodiments. In other words, as long as the present invention can be put into practice, a person skilled in the art may choose some or all of the technical features in any of the embodiments or combine some or all of the technical features in different embodiments based on the teachings herein and depending on relevant design specifications or the requirements of practical applications. In this way, the present invention can be carried out more flexibly.

As used herein, the singular forms "a", "an" and "the" include plural referents, unless the context clearly dictates otherwise. As used herein, the term "a plurality of" means two or more than two, unless the context clearly dictates otherwise. As used herein, the term "or" is employed in the sense including "and/or" unless the context clearly dictates otherwise. Additionally, it is to be noted that reference numerals and/or characters may be repeatedly used throughout the embodiments disclosed hereafter. Such repeated use is intended for simplicity and clarity and does not imply any relationship between the discussed embodiments and/or configurations. It is to be also noted that when a component is described herein as being "connected" to another component, it may be connected to the other component either directly or via one or more intervening elements.

In general terms, the present invention seeks to provide an electrode plate primarily for use in cardiac defibrillation. The electrode plate includes a hermetic shell and a capsule housed in the hermetic shell. The hermetic shell has an inflation port and an overflow aperture (a paste-overflow aperture). The overflow aperture is provided in an exposed surface of the hermetic shell, which is conductive. The capsule defines a cavity for store therein a conductive paste. The cavity defines an inlet orifice and an outlet orifice. The overflow aperture is disposed at the outlet orifice, and the cavity is isolated from a hollow internal space of the hermetic shell. The electrode plate further includes a sealing structure, which includes a sealing component and a force applying component. The sealing component is disposed at the overflow aperture and configured to close the overflow aperture and the outlet orifice when the hermetic shell is not inflated. The force applying component is disposed on the hermetic shell so as to be passed through the capsule via the inlet orifice thereof and coupled to the sealing component. The force applying component is configured to, as a result of inflation and expansion of the hermetic shell, pull the sealing component to open the overflow aperture and the outlet orifice so that they come into communication with each other.

During use of the electrode plate, when no gas is introduced into the hermetic shell, without being subjected to a pulling force from the force applying component, the sealing component blocks the overflow aperture and maintains it in the closed configuration, where the overflow aperture does not communicate with the outlet orifice and the conductive paste is prevented from being released. When a gas is introduced into the hermetic shell through the inflation port, under the effect of expansion of the hermetic shell, the force applying component pulls the sealing component and completely or partially separates it from the overflow aperture, placing it into the open configuration, where it is in communication with the outlet orifice, thereby releasing the conductive paste, under the action of a gas pressure, the conductive paste overflows from the outlet orifice and flows onto the exposed surface through the overflow aperture. Here, the exposed surface is configured to be brought into contact with the patient's skin, and therefore the conductive paste filled between the patient's skin and the exposed surface effects an impedance drop.

The electrode plate of the present invention enables automated application of the conductive paste, which helps a wearable defibrillation device to provide the patient with timely protection. Moreover, the overflow aperture can be opened in a safer and more reliable manner, compared to causing breakage of the capsule by explosion of a gas-producing agent. In addition, the hermetic shell of the electrode plate can be designed sufficiently lightweight and slim to increase wearing comfort and compliance. Further, since the electrode plate of the present invention is a disposable product, it is inexpensive and can relieve the patient's treatment burden.

The electrode plate and wearable defibrillation device provided in the present invention will be further described below with reference to the accompanying drawings which present several preferred embodiments of the invention.

Embodiment 1

Figure 2:
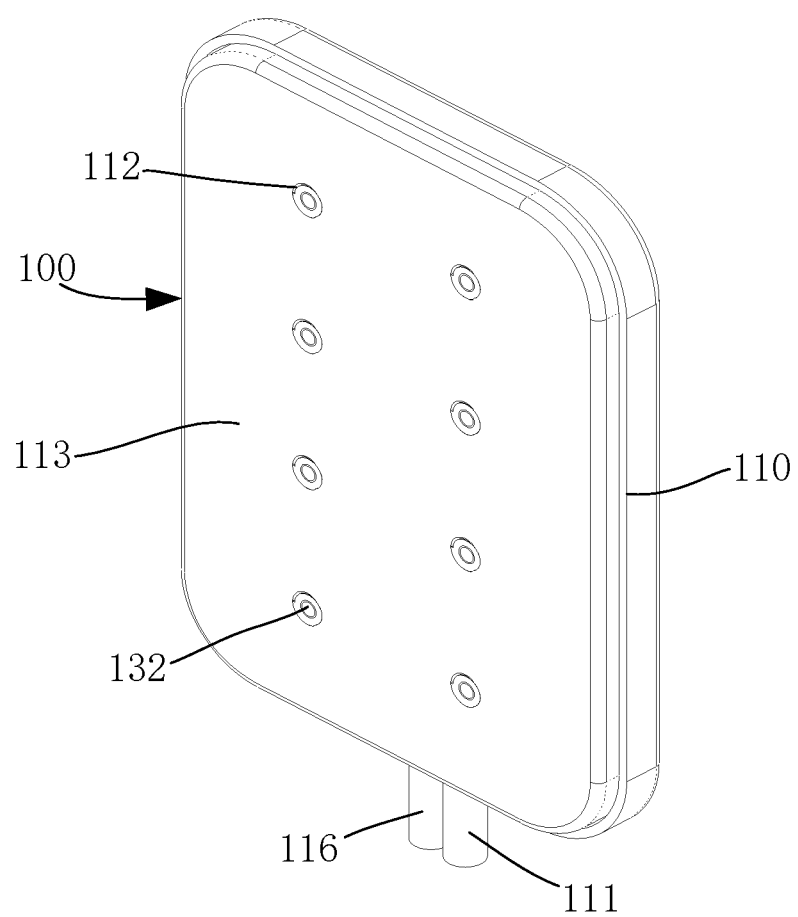
FIG. 2 is a schematic assembled view of an electrode plate according to a first embodiment of the present invention.
Figure 3:
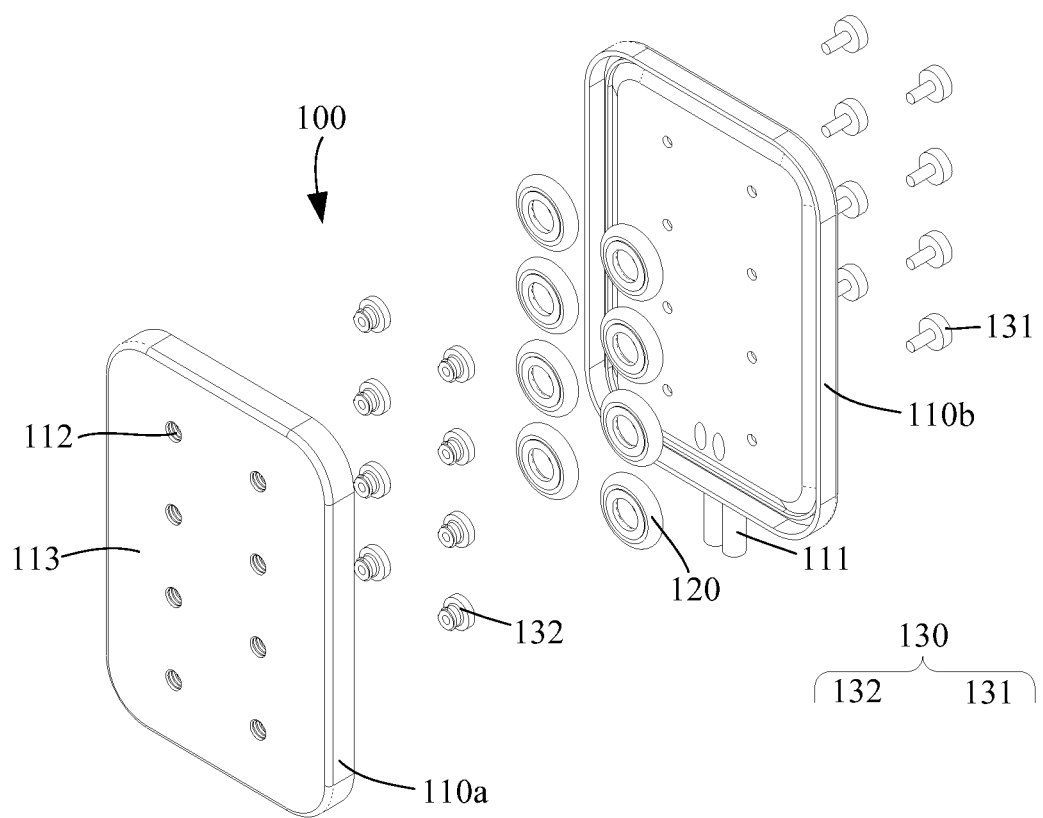
FIGS. 3 to 4 are schematic exploded views of the electrode plate according to the first preferred embodiment of the present invention.
Figure 4:
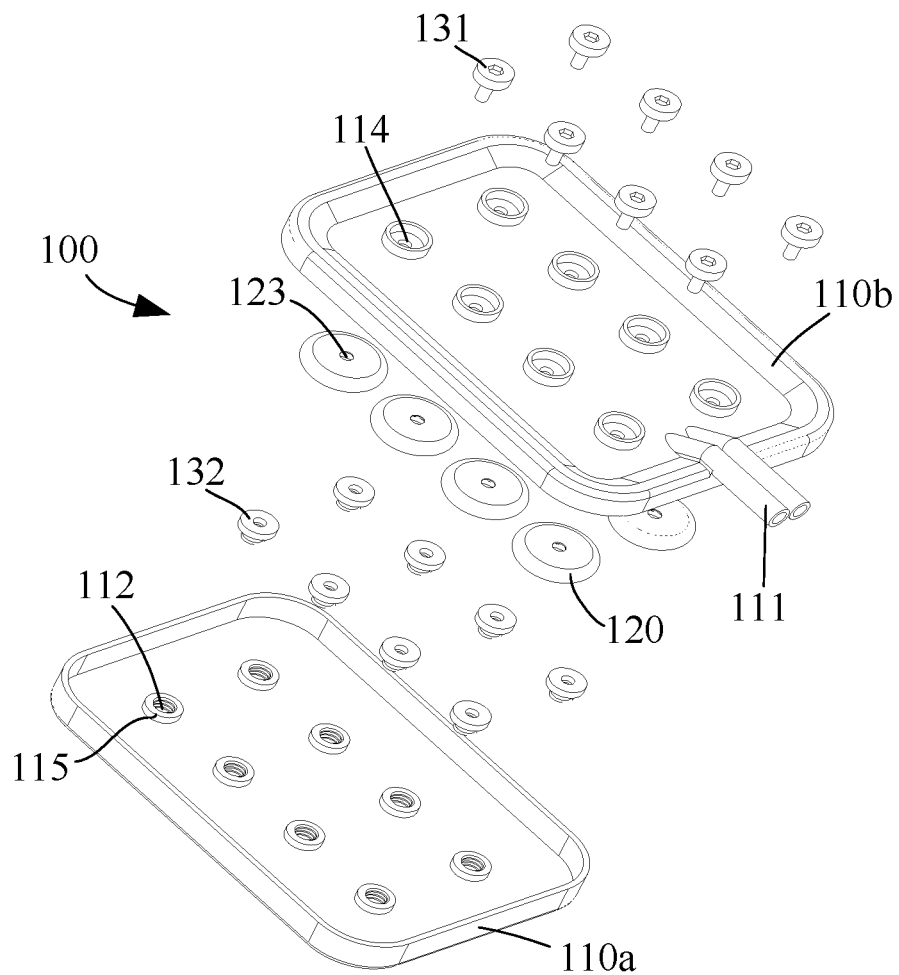
Figure 5:
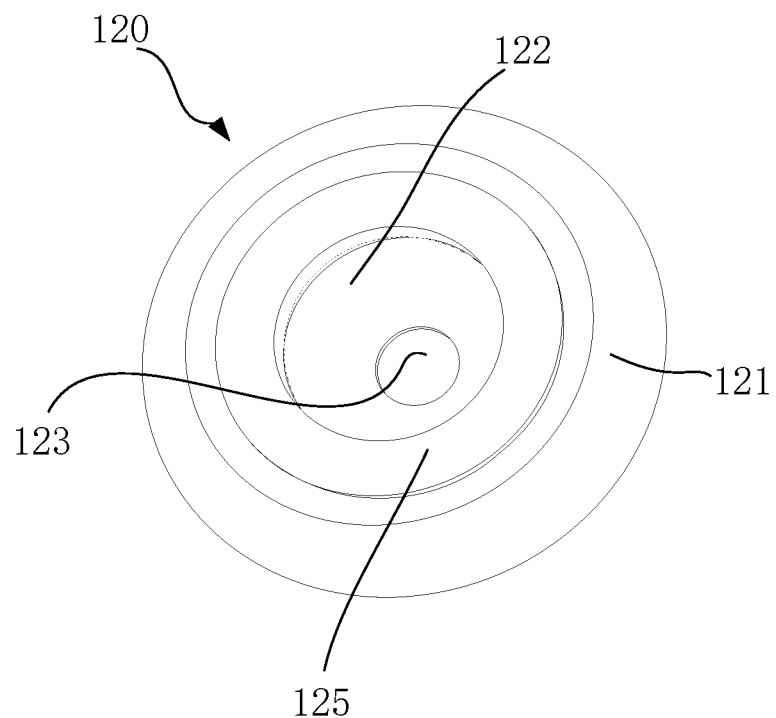
FIG. 5 is a schematic three-dimensional diagram of a capsule according to the first preferred embodiment of the present invention.
Figure 6:
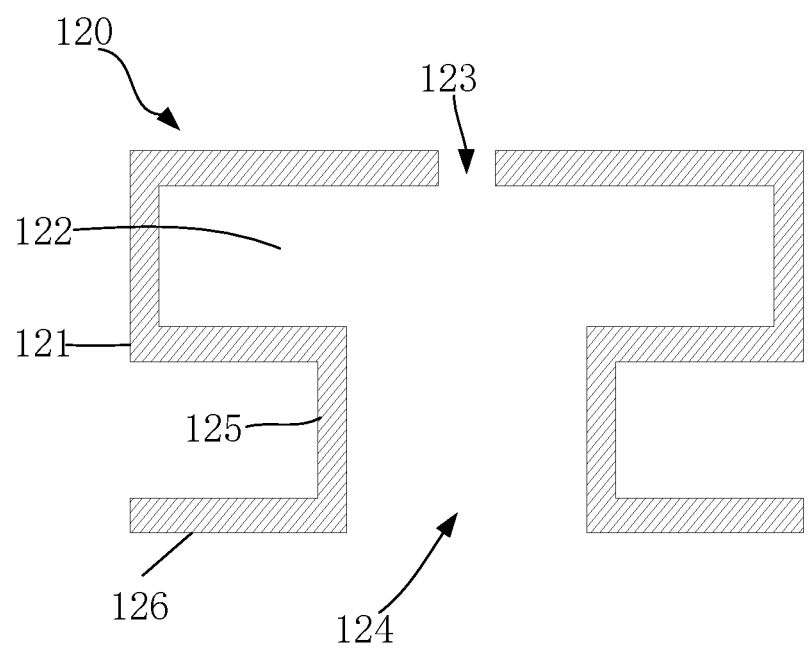
FIG. 6 is a cross-sectional view of the capsule according to the first preferred embodiment of the present invention.

FIG. 2 is a schematic assembled view of an electrode plate according to a preferred embodiment of the present invention. FIGS. 3 and 4 are schematic exploded views of the electrode plate according to the preferred embodiment of the present invention. FIG. 5 is a three-dimensional diagram of a capsule according to the preferred embodiment of the present invention. FIG. 6 is a cross-sectional view of the capsule according to the preferred embodiment of the present invention.

As shown in FIGS. 2 to 4, the electrode plate 100 of the present embodiment is intended mainly for use in cardiac defibrillation and includes a hermetic shell 110 and capsule 120. The capsule 120 is disposed within the hermetic shell 110 and configured for storage of a conductive paste therein. As shown in FIGS. 5 to 6, the capsule 120 includes a body 121, the body 121 defines a hollow cavity 122 in which the conductive paste is stored. The cavity 122 defines an inlet orifice 123 and an outlet orifice 124. The conductive paste is injected into the capsule 120 via the inlet orifice 123 and released therefrom via the outlet orifice 124.

Referring back to FIGS. 2 to 4, the hermetic shell 110 has an inflation port 111 and an overflow aperture 112. Through the inflation port 111, external gas (preferably air) can be passed into the hermetic shell 110. In this embodiment, the hermetic shell 110 may be inflated using an inflation pump included in a wearable defibrillation device, which can provide relatively safe inflation pressure. The overflow aperture 112 is disposed in an exposed surface 113 of the hermetic shell 110, the exposed surface 113 is conductive and intended to be brought into contact with the patient's skin. The capsule 120 is secured in the hermetic shell 110 in correspondence with the overflow aperture 112 so that the outlet orifice 124 of the capsule 120 is aligned with the overflow aperture 112 to allow release of the conductive paste through the overflow aperture 112. Here, the present invention is not limited to how the capsule 120 is secured. For example, the capsule 120 may be glued to an inner wall of the hermetic shell 110. Preferably, a capsule receptacle (not shown) may be provided on the inner wall of the hermetic shell 110. In this case, the capsule 120 may be seated in and glued to the capsule receptacle. In this way, the capsule 120 can be secured firmly, which is not easy to fall off during use.

The electrode plate 100 further includes a sealing structure 130, the sealing structure 130 includes a force applying component and a sealing component. In this embodiment, the force applying component is a fastening screw 131, and the sealing component is a sealing screw 132. Additionally, the overflow aperture 112 is an internally threaded bore. In practical use, the sealing screw 132 is screwed into the overflow aperture 112 and threadedly tightened in a sealing manner. Subsequently, the capsule 120 is fitted outside of the sealing screw 132, and the fastening screw 131 is then inserted and tightened into the sealing screw 132. More specifically, the fastening screw 131 is passed successively through a mounting hole 114 in the hermetic shell 110 and the inlet orifice 123 of the capsule 120 into the capsule 120 and then threadedly tightened in the sealing screw 132. In other words, part of the fastening screw 131 is received in the mounting hole 114 of the hermetic shell 110 (see FIG. 4), and the rest is inserted through the inlet orifice 123 of the capsule 120 into the capsule 120 and then threadedly tightened in the sealing screw 132. In this way, the overflow aperture 112 may assume either a closed configuration or an open configuration. When no gas is introduced into the hermetic shell 110, without being subjected to a pulling force from the fastening screw 131, the sealing screw 132 remains tightened in the overflow aperture 112, maintaining the overflow aperture 112 in the closed configuration, where the conductive paste is prevented from being released from the capsule 120. On the contrary, when a gas is introduced into the hermetic shell 110 through the inflation port 111, under the effect of expansion of the hermetic shell 110, the fastening screw 131 starts to pull the sealing screw 132, and when the pulling force increases to a certain level, the sealing screw 132 is separated from the overflow aperture 112, placing the overflow aperture 112 into the open configuration, where the cavity 122 of the capsule 120 is in direct communication with the overflow aperture 112, allowing the conductive paste in the capsule 120 to overflow from the outlet orifice 124 in the capsule 120 under the action of a gas pressure and flow through the overflow aperture 112 into a gap between the exposed surface 113 and the patient's skin to effect an impedance drop. At this point, the electrode plate 100 may deliver a high DC voltage for defibrillation treatment. The mounting hole 114 for receiving the fastening screw 131 is provided in a surface of the hermetic shell 110 that is opposite to the exposed surface 113. It would be appreciated that the force applying component is not limited to being threadedly coupled to the sealing component. In other embodiments, the force applying component may be coupled to the sealing component by an interference fit or glue. Likewise, the sealing component is not limited to being threadedly coupled to the overflow aperture 112 because it may also be coupled thereto by an interference fit or glue. Since the electrode plate 100 is a disposable product, a non-detachable connection which cannot be reestablished once destroyed is also possible. The present invention is not limited to any particular materials of the fastening screw 131 and the sealing screw 132, and both metallic and non-metallic materials are possible. It is to be understood that the sealing screw 132 should be configured with good sealing performance that ensures no leakage of the conductive paste even when under pressure. Moreover, it would be appreciated that, as the cavity 122 of the capsule 120 is isolated from the hollow internal space of the hermetic shell 110, the conductive paste that has exited the outlet orifice 124 of the capsule 120 will not enter the interior of the hermetic shell 110, and when the overflow aperture 112 is opened, a press drop will not occur within the hermetic shell 110. Thus, hermeticity of the hermetic shell 110 can be ensured.

In this embodiment, the hermetic shell 110 is provided on the inner wall with a threaded boss 115 (see FIG. 4) defining an internally threaded bore configured as the overflow aperture 112. Specifically, the threaded boss 115 projects from the exposed surface 113 toward the interior of the hermetic shell 110 (see FIG. 4), and the internally threaded bore axially extends through the threaded boss 115. The threaded boss 115 extends through the outlet orifice 124 of the capsule 120 into the interior of the capsule 120, and the capsule 120 is sealingly coupled to the threaded boss 115. During practical assembly, the overflow aperture 112 can be sealed simply by inserting the sealing screw 132 into the threaded boss 115 and threadedly coupling it to the hermetic shell 110 in a sealing manner. This entails a simple structure and easy operation. After the sealing screw 132 is sealingly tightened in the threaded boss 115, the capsule 120 is fitted outside of the threaded boss 115, and a sealing coupling is then established between the capsule 120 and the threaded boss 115. Additionally, the exposed surface 113 may be provided thereon with a terminal post (not shown), and an external lead cable connected to the host 400 described below may be tied to the terminal post to enable the supply of an electric current.

Figure 14:
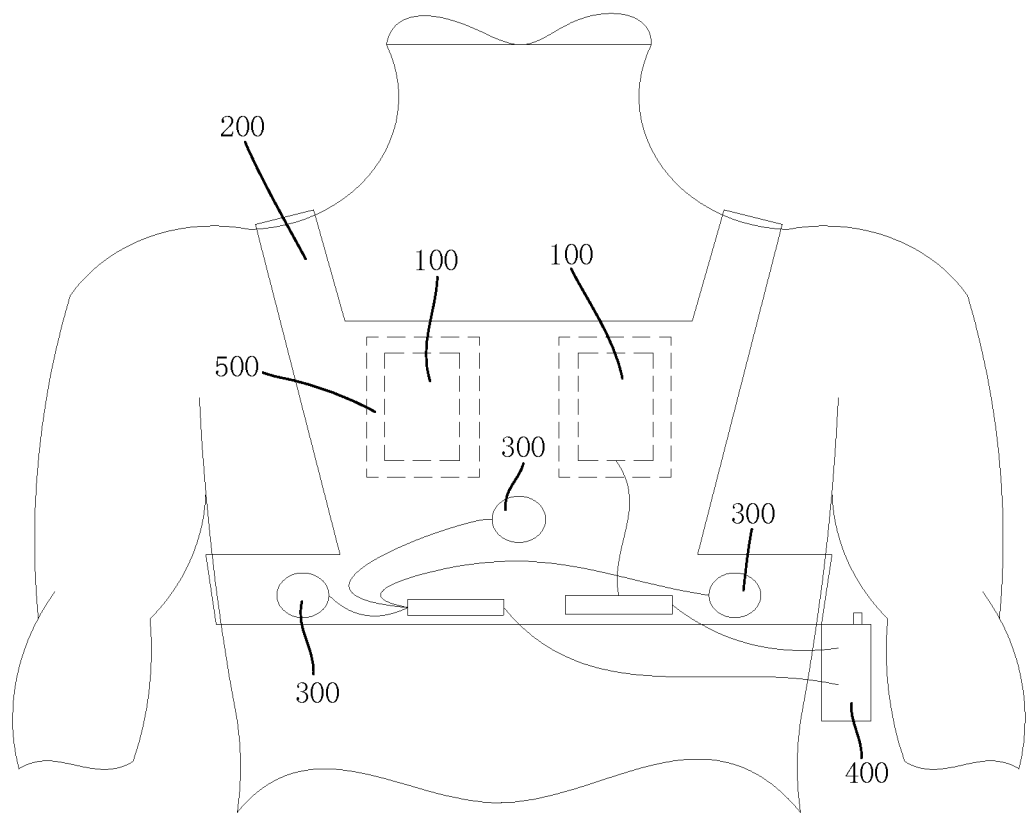
FIG. 14 explains how a wearable defibrillation device according to the first preferred embodiment of the present invention is used.

As shown in FIG. 14, in this embodiment, there is also provided a wearable cardioverter-defibrillator (WCD) device including a vest 200 and, provided on the vest 200, the electrode plate 100, a sensing electrode 300, a host 400 and an airbag 500. With reference to FIG. 14, in practical use, the vest 200 is worn on the patient, and the operating principle of the WCD device is that the sensing electrode 300 senses an ECG signal and feeds the ECG signal to the host 400. The host 400 responsively produces an electrocardiogram and makes a determination based thereon. If the host 400 determines that the patient is in need of defibrillation, the airbag 500 and the electrode plate 100 are inflated. The inflated airbag 500 compresses the electrode plate 100 against the patient's skin, and the inflation of the electrode plate 100 causes the hermetic shell 110 to expand and exert a pulling force on the fastening screw 131. As an internal pressure within the hermetic shell 110 rises, the sealing screw 132 will be ultimately separated from the threaded boss 115, thus opening the overflow aperture 112. Consequently, the conductive paste contained in the capsule 120 is urged by the gas pressure to flow out thereof through the overflow aperture 112 on the hermetic shell 110 into a gap between the exposed surface 113 and the patient's skin, effectuating an impedance drop. When this happens, the electrode plate 100 can deliver a high DC voltage for defibrillation treatment. It is to be understood that the electrode plate 100 and the airbag 500 may be inflated simultaneously or successively, without limiting the present invention in any away, with simultaneous inflation being more preferred. More preferably, the electrode plate 100 also functions as the airbag 500. In this way, the use of a separate airbag is dispensed with, and the electrode plate 100 can be compressed against the patient's skin and the conductive paste can be released, simply by inflating the electrode plate 100. This makes the defibrillation device simpler in structure and easier to operate. It is also to be understood that the overflow aperture 112 may be opened as a result of either complete or partial separation of the sealing screw 132 from the overflow aperture 112. By "partial separation of the overflow aperture 112", it is intended to mean that the conductive paste can be released as long as there is a leakage gap between the sealing screw 132 and the overflow aperture 112.

It is to be understood that structural strength of the hermetic shell 110 of the present invention should suffice to prevent the electrode plate 100 from experiencing defibrillation performance degradations due to its deformations that occur when it is compressed or twisted during physical activities of the patient during his/her daily wearing and to prevent the capsules 120 therein from being accidentally compressed and broken. On the other hand, the hermetic shell 110 should also have sufficient flexibility, which ensures that it will expand when inflated. This effectuates inflation pressure drops, which ensure safety and reliability of the inflation process and enhances the patient's wearing comfort and compliance. For these reasons, the hermetic shell 110 is structurally configured with both sufficient strength and a certain degree of flexibility. Therefore, the use of the electrode plate 100 enables the WCD device to operate in a fully automated way, which facilitates timely protection of the patient. Moreover, before the defibrillation action is taken by the electrode plate 100, automatic application of the conductive paste is achieved to effectively ensure sufficiently low contact resistance between the electrode plate 100 and the skin, which ensures safe and effective defibrillation. Further, the electrode plate 100 is a low-cost disposable product, and its use can relieve the patient's burden for surgery.

In this embodiment, the hermetic shell 110 includes a defibrillation panel 110a and a rear shell member 110b (see FIG. 3), which are coupled together to form an enclosed casing. An external surface of the defibrillation panel 110a serves as the exposed surface 113, and the capsule 120 is secured to the defibrillation panel 110a on the side thereof facing the rear shell member 110b. The defibrillation panel 110a and the rear shell member 110b may be glued together. Preferably, material strength of the defibrillation panel 110a is higher than that of the rear shell member 110b. In this way, the defibrillation panel 110a enables the electrode plate 100 to have sufficient strength, while the rear shell member 110b enables the electrode plate 100 to have sufficient flexibility. Moreover, the relatively pliable rear shell member 110b can effectuate inflation pressure drops to ensure safe and reliable inflation. The present invention is not limited to any particular materials of the defibrillation panel 110a and the rear shell member 110b, as long as the rear shell member 110b can provide insulating properties and the exposed surface 113 of the defibrillation panel 110a is conductive. As a non-limiting example, the defibrillation panel 110a may be fabricated from conductive rubber, or provided as an insulating rubber/metal sheet or metallic material/plastic composite structure. The rear shell member 110b is made of a soft material, examples of which may include, but are not limited to, rubber, PVC and TPU.

In order to facilitate control of an amount of deformation of the rear shell member 110b, which imparts controllability to the process of pulling the sealing screw 132 to open the overflow aperture 112 and allows for more reliable and convenient release of the conductive paste, the rear shell member 110b is preferably provided on an inner surface thereof with a bump (not labeled) protruding toward the defibrillation panel 110a, or the rear shell member 110b is provided on an inner surface thereof with annular corrugations (not shown), or provided with both the bump and the annular corrugations. Preferably, the electrode plate 100 further includes a reinforcing plate (not shown) disposed on the side of the rear shell member 110b away from the defibrillation panel 110a. The reinforcing plate is attached to the rear shell member 110b to provide support to the rear shell member 110b. The reinforcing plate may be either a metallic or non-metallic material.

In some embodiments, the defibrillation panel 110a is a two-piece component consisting of a conductive panel and a front shell member. The front shell member is an insulator, while the conductive panel is a conductor. In this case, the front shell member and the rear shell member 110b are coupled together to form an enclosed casing, and the conductive panel provides the exposed surface 113 and is disposed on the side of the front shell member away from the rear shell member 110b. Moreover, the capsule 120 is attached to the front shell member, and the overflow aperture 112 may consist of two portions, one of which is disposed on the conductive panel, and the other on the front shell member. Preferably, material strength of the front shell member is higher than that of the rear shell member. In practical operation, the conductive panel may be glued to the front shell member, and the conductive panel may be formed of conductive rubber or a metal plate that is less costly. The front shell member may be made of a metallic or non-metallic material. A non-limiting example of the non-metallic material is plastic. In other embodiments, the conductive panel may be omitted. In this case, the defibrillation panel is made up of only the front shell member, and at least the exposed surface 113 of the front shell member is conductive.

The present invention is not limited to any particular material of which the capsule 120 is made, and examples of the material may include, but are not limited to, silica gel, latex, TPU, etc. The capsule 120 may be made either integrally or separately. With additional reference to FIGS. 5 and 6, the capsule 120 is preferred to further include a collar 125 extending outward from the body 121. The collar 125 defines a hollow channel providing the outlet orifice 124. In this case, the collar 125 of the capsule 120 may be fitted over the threaded boss 115. Additionally, the collar 125 may have a footing support 126, which extends outward therefrom and extends around an axis thereof. The footing support 126 is disposed on the inner wall of the hermetic shell 110, accomplishing attachment of the capsule 120. Here, the collar 125 can enhance crush resistance of the capsule 120, preventing it from being damaged by accident. Further, the capsule 120 may be designed with annular corrugations to increase its amount of deformability, preventing it from being ruptured when pulled.

Figure 7:
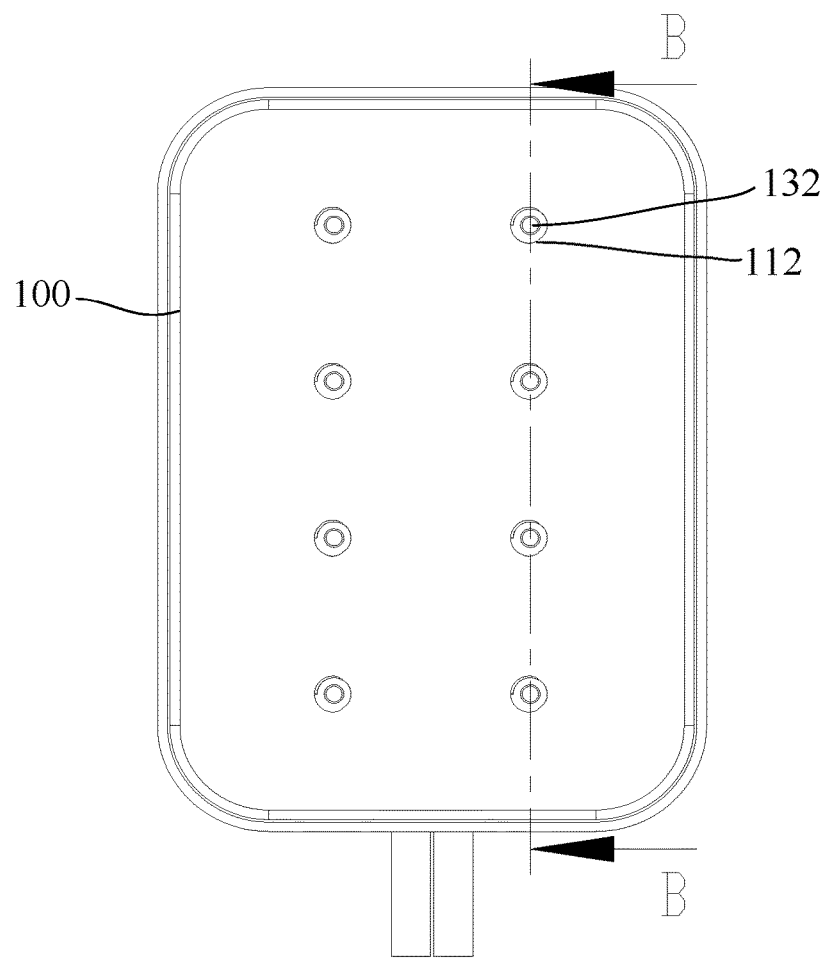
FIG. 7 is a front view of the electrode plate according to the first preferred embodiment of the present invention, showing cross-sectional line B-B.
Figure 8:
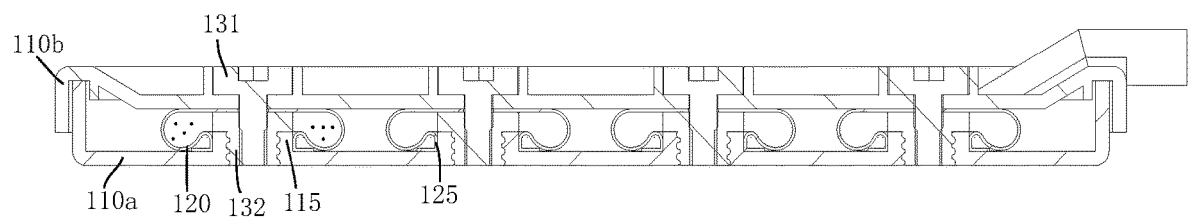
FIG. 8 is a cross-sectional view of the electrode plate in FIG. 7 taken along line B-B.

Reference is now made to FIGS. 7-8, FIG. 7 is a front assembled view of the electrode plate according to a preferred embodiment of the present invention, and FIG. 8 is a cross-sectional view taken along line B-B in FIG. 7. An internal bore of the collar 125 (i.e., the aforementioned channel) is fitted over the threaded boss 115, and before the sealing screw 132 is inserted into the threaded boss 115, the internally threaded bore (i.e., the overflow aperture 112) of the threaded boss 115 is in direct communication with the cavity 122 of the capsule 120. When the sealing screw 131 is inserted into the threaded boss 115, the internally threaded bore of the threaded boss 115 is occluded. Afterward, through inserting the fastening screw 131 into the capsule 120 and coupling it to the sealing screw 132, the inlet orifice 123 of the capsule 120 can be closed. In this embodiment, the collar 125 may be made either integrally with or separately from the body 121. Further, in order to prevent from the capsule 120 from falling off when pulled, a protrusion (not shown) may be provided on an inner wall of the rear shell member 110b for firmly compressing and holding the capsule 120. The protrusion may be fabricated integrally with or separately from the rear shell member 110b, with separate fabrication being more preferred because of lower fabrication cost. Optionally, the protrusion may be a flat gasket glued to the rear shell member 110b.

Figure 9:
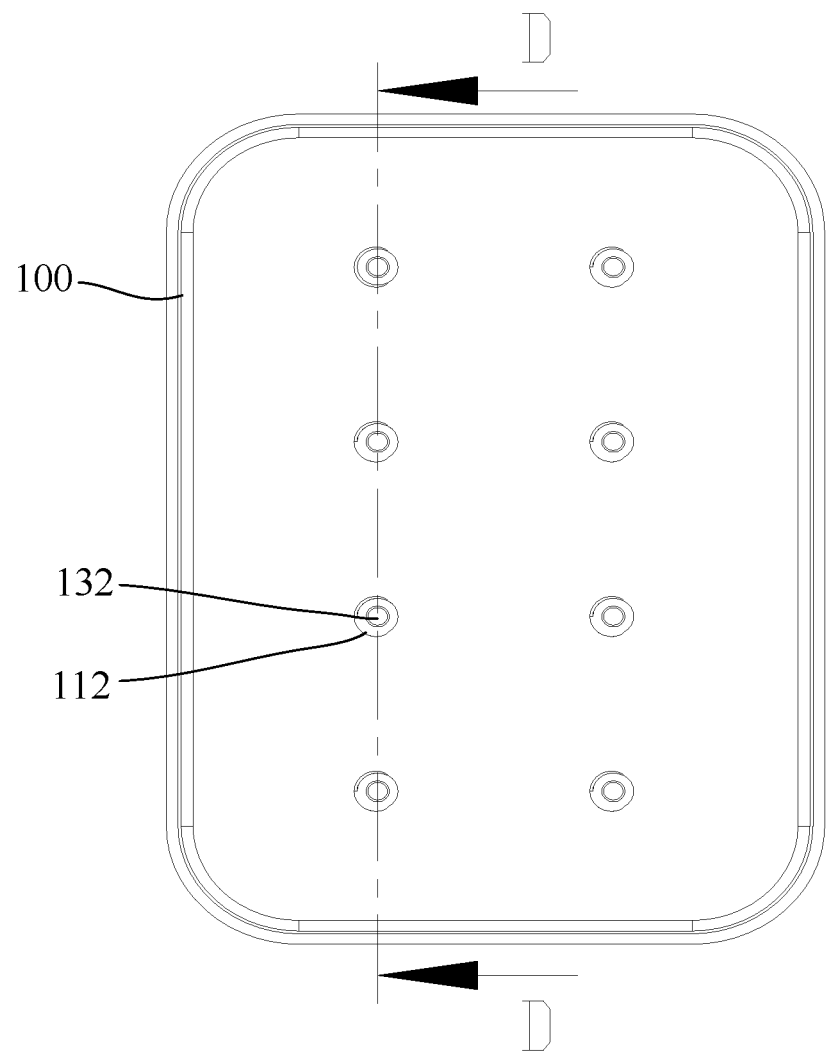
FIG. 9 is another front view of the electrode plate according to the first preferred embodiment of the present invention, showing cross-sectional line D-D.
Figure 10:
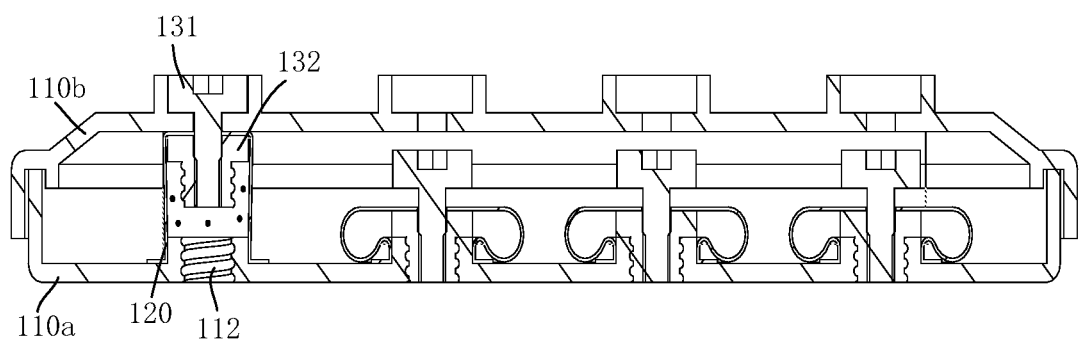
FIG. 10 is a cross-sectional view of the electrode plate in FIG. 9 taken along line D-D.
Figure 11:
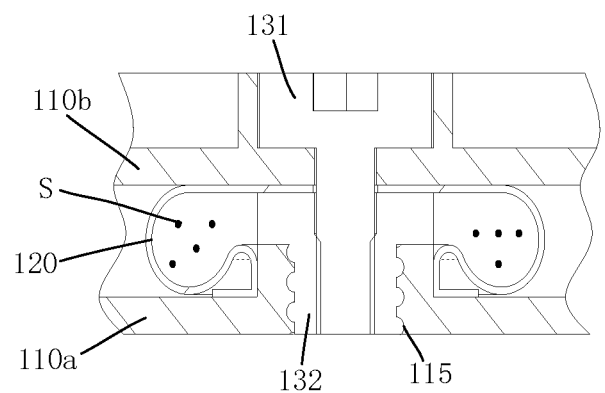
FIG. 11 is an enlarged partial view of the electrode plate of FIG. 8.
Figure 12:
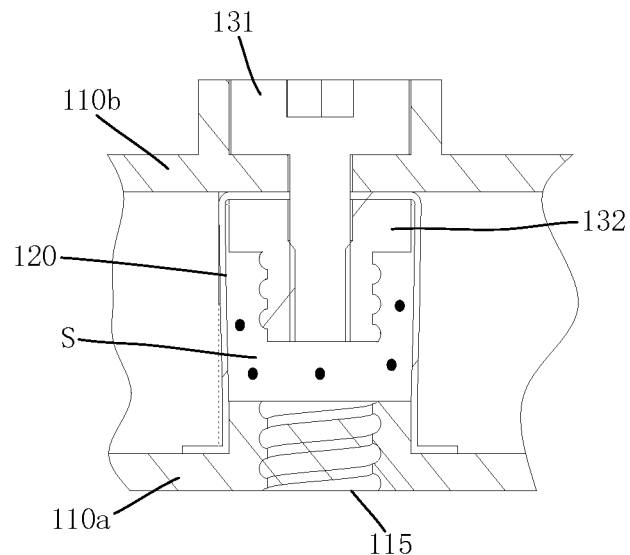
FIG. 12 is an enlarged partial view of the electrode plate of FIG. 10.

Reference is now made to FIGS. 9-10, FIG. 9 is a front assembled view of the electrode plate according to a preferred embodiment of the present invention, and FIG. 10 is a cross-sectional view taken along line D-D in FIG. 9. Wherein, a plurality of capsules 120 are included, and for ease of understanding, it is assumed in FIG. 10 that some of the sealing screws 132 have been pulled off, while the others are not, showing differences between these configurations in use. With additional reference to the enlarged partial views of FIGS. 11 and 12, when the host 400 determines that the patient is in need of defibrillation, the electrode plate 100 is inflated. As a gas pressure therein increases, the hermetic shell 110 will gradually expands, thus enlarging the distance between the defibrillation panel 110a and the rear shell member 110b. As a result, the sealing screw(s) 132 is/are subjected to a pulling force. Since the defibrillation panel 110a is rather flexible, when the pulling force increases to a certain level, the sealing screw 132 will be pulled out of the threaded boss 115 of the defibrillation panel 110a, thereby opening the overflow aperture 112 and bringing it into communication with the outlet orifice 124. After that, the capsule 120 is elongationally deformed, and the conductive paste S is squeezed out thereof by the gas pressure.

Preferably, a plurality of, i.e., two or more, capsules 120 may be included. In this case, the present invention is not limited to any particular number of capsules 120, and as long as allowed by the accommodating space, as many as possible capsules 120 may be arranged therein, in order to attain an increased amount of released conductive paste, a larger coated area and higher defibrillation safety. Moreover, each capsule 120 may be configured with a respective overflow aperture 112. In this way, the conductive paste may be caused to flow out of the capsules 120 from the respective overflow apertures 112. It is to be understood each capsule 120 is configured in the above-described manner, and the capsules 120 are not limited to being arranged in any particular way. As a non-limiting example, they may be arranged into N rows and M columns, as shown in the figures, where both N and M are positive integers. It is also to be understood, in case of multiple capsules 120 being included, as the cavities 122 of the capsules 120 are isolated from the hollow internal space of the hermetic shell 110, even when any overflow aperture 112 is opened, no press drop that may make the remaining capsules 120 impossible to be opened anymore will occur within the hermetic shell 110, ensuring reliable release of the conductive paste.

Referring back to FIGS. 2 to 4, the hermetic shell 110 further includes a cable port 116, which facilitates external lead cable to enter and exit the hermetic shell 110 through the cable port 116, thereby providing an electric current to the defibrillation panel 110a. The cable port 116 is preferably arranged in the vicinity of the inflation port 111. The present invention is not limited to any particular shape of the hermetic shell 110. It may be the rectangular parallelepiped as shown in the figures, or another hexahedral or profiled shape. Further, in the present invention, the pressure of a gas filled in the hermetic shell 110 may be controlled within a preset value in order to prevent its breakage due to overpressure, which may cause injury to the patient or failure of defibrillation.

Figure 13:
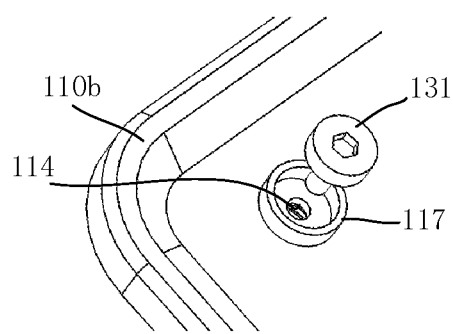
FIG. 13 is an enlarged partial view of a rear shell member according to the first preferred embodiment of the present invention.

Reference is now made to FIG. 13, a schematic partial view of the rear shell member according to a preferred embodiment of the present invention. The rear shell member 110b is provided therein with an injection port, through which the conductive paste is injected to the capsule 120. The mounting hole 114 may serve as the injection port. In practical operation, the conductive paste may be conveniently injected into the capsule 120 within a short time through the mounting hole 114 simply using a syringe. After the injection is completed, the conductive paste can be prevented from leakage simply by deploying the fastening screw 131 in the mounting hole 114 in a sealing manner. Preferably, a screw receptacle 117 for accommodating a head of the fastening screw 131 and thereby effectively preventing the fastening screw 131 from falling off is formed around the mounting hole 114. The screw receptacle 117 may be defined by a wall which protrudes outward and extends circumferentially around the mounting hole 114.

Embodiment 2

Figure 15:
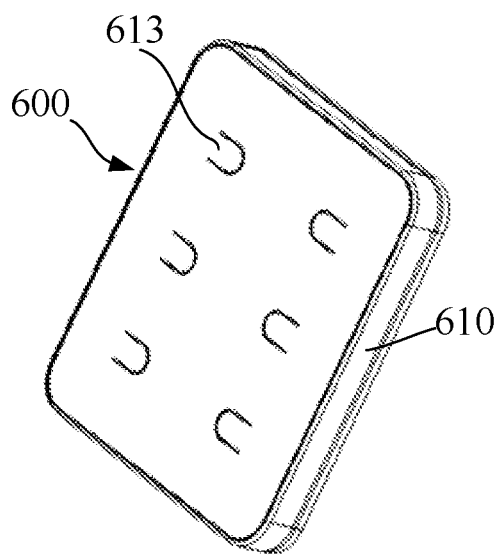
FIG. 15 is a schematic assembled front view of an electrode plate according to a second embodiment of the present invention, in which a barrier sheet has not been torn open yet.
Figure 16:
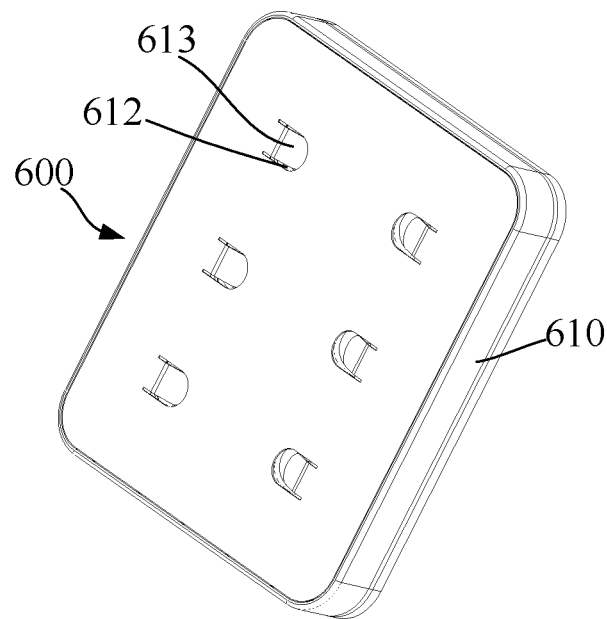
FIG. 16 is another schematic assembled front view of the electrode plate according to the second embodiment of the present invention, in which the barrier sheet has been already torn open.
Figure 17:
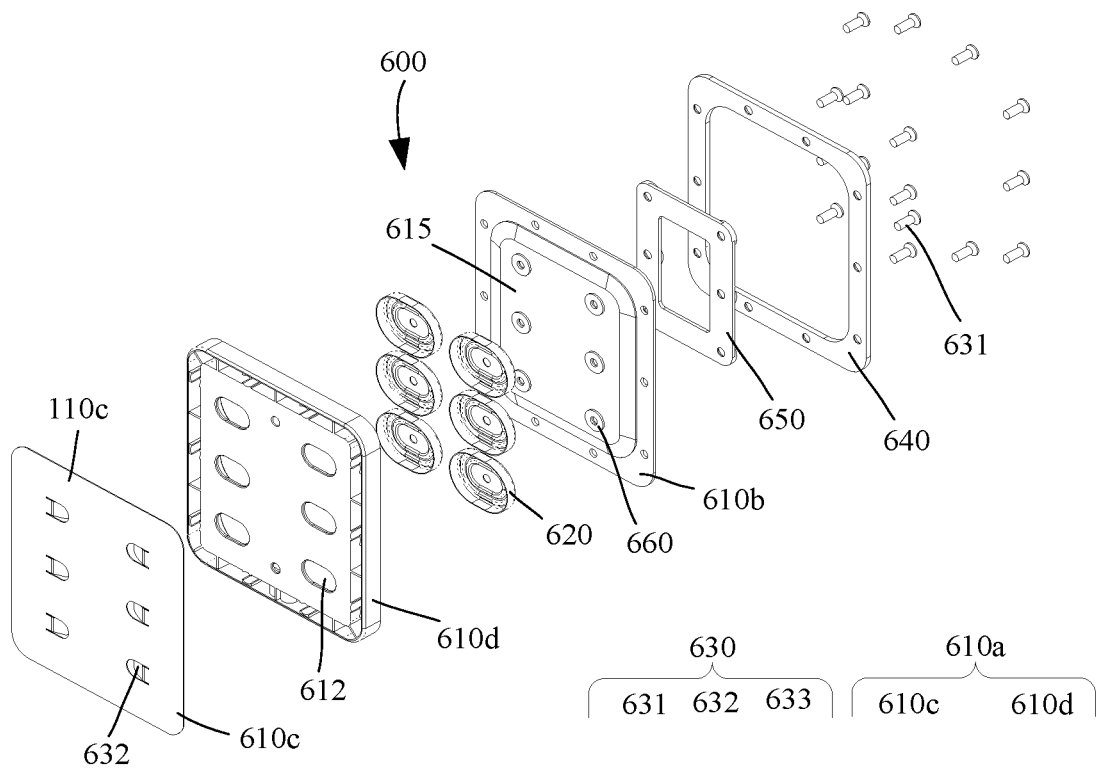
FIG. 17 is a schematic exploded view of the electrode plate according to the second embodiment of the present invention.
Figure 18:
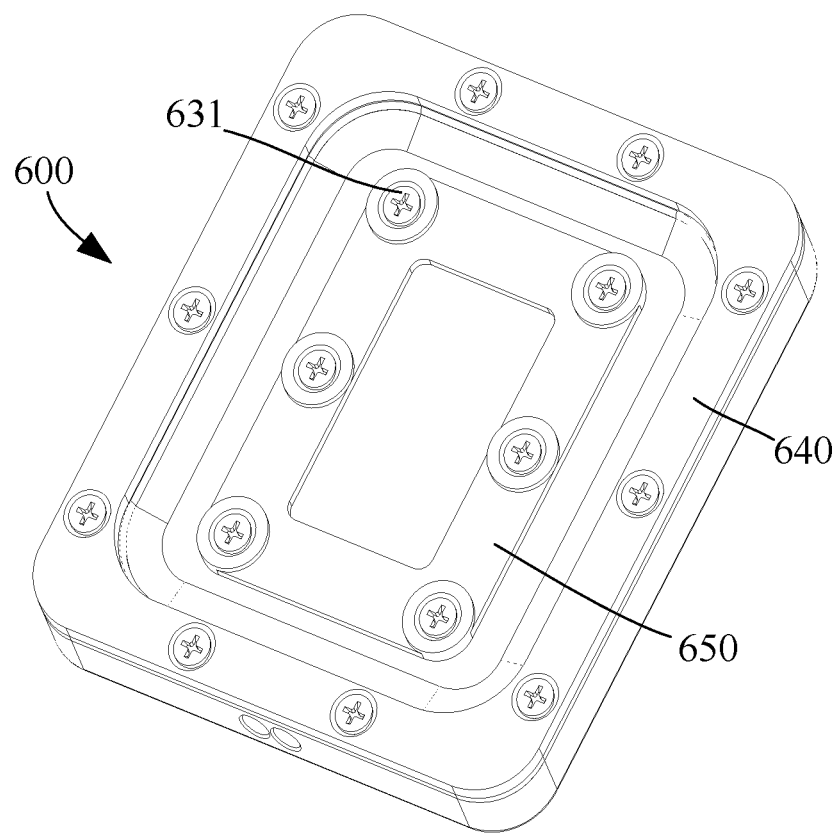
FIG. 18 is a schematic assembled back view of the electrode plate according to the second embodiment of the present invention.

FIGS. 15 to 16 are schematic assembled views of an electrode plate according to a preferred embodiment of the present invention. FIG. 17 is a schematic exploded view of the electrode plate according to the preferred embodiment of the present invention. FIG. 18 is an assembled three-dimensional diagram of the electrode plate according to the preferred embodiment of the present invention. As shown in FIGS. 15 to 18, the electrode plate 600 in the present embodiment includes a hermetic shell 610 and a capsule 620. The capsule 620 is disposed within the hermetic shell 610 and configured for storage of a conductive paste therein. Essentially similar to the first embodiment, the capsule 620 includes a body defining a hollow cavity. The cavity defines an inlet orifice and an opposing outlet orifice. The conductive paste can be injected into the capsule 620 through the inlet orifice and released through the outlet orifice. The capsule 620 may be glued to a defibrillation panel 610a, and a through overflow aperture 612 may be provided in an inner wall of the defibrillation panel 610a. The overflow aperture 612 communicates with the cavity of the capsule 620 through the outlet orifice of the capsule 620.

The electrode plate 600 further includes a sealing structure 630, the sealing structure 630 includes a force applying component and a sealing component. In this embodiment, the force applying component is a fastening screw 631, and the sealing component includes a barrier sheet 632 and a connecting member. The connecting member is preferred to be a threaded boss 633. Threaded boss 633 extends through the outlet orifice of the capsule 620 into the interior of the capsule 620 and defines threaded blind bore for preventing leakage. In the exemplary context of the threaded boss 633, the threaded boss 633 is provided on the barrier sheet 632, the barrier sheet 632 is provided on the defibrillation panel 610a so as to cover the overflow aperture 612, that is, the barrier sheet 632 closes the overflow aperture 612. In practical use, part of the fastening screw 631 is disposed in a mounting hole of a rear shell member 610b, and the rest is inserted through the inlet orifice of the capsule 620 into the capsule 620 and threadedly tightened in the threaded boss 633. In this way, the overflow aperture 612 may assume either a closed configuration or an open configuration. When no gas is introduced into the hermetic shell 610, the threaded boss 633 is not subjected to a pulling force from the fastening screw 631, and the barrier sheet 632 is not broken open and closes the overflow aperture 612, maintaining the overflow aperture 612 in the closed configuration where the conductive paste is prevented from being released. On the contrary, when a gas is introduced into the hermetic shell 610 through an inflation port, under the effect of expansion of the hermetic shell 610, the fastening screw 631 pulls the threaded boss 633 and hence the barrier sheet 632 via the threaded boss 633. As a result, the barrier sheet 632 is broken open, placing the overflow aperture 612 into the open configuration, at this time, the conductive paste is urged by a gas pressure to flow out of the outlet orifice of the capsule 620 and to flow through the overflow aperture 612 into a gap between an exposed surface and a patient's skin to effect an impedance drop. At this point, the electrode plate 600 may deliver a high DC voltage for defibrillation treatment. It is to be understood that in other embodiments, the force applying component may be coupled to the connecting member by an interference fit or glue, while achieving a similar effect. It is also to be understood that, according to this embodiment, the covering of the overflow aperture 612 by the barrier sheet 632 may include coupling thereof to the overflow aperture 612. In this case, as long as the barrier sheet 632 remains coupled to the overflow aperture 612, the barrier sheet 632 covers the overflow aperture 612. However, upon the barrier sheet 632 being disconnected from the overflow aperture 612, the barrier sheet 632 no longer covers the overflow aperture 612 and the overflow aperture 612 is exposed.

In this embodiment, the hermetic shell 610 includes the defibrillation panel 610a and the rear shell member 610b. The defibrillation panel 610a may further include a conductive panel 610c and a front shell member 610d. The front shell member 610d and the rear shell member 610b are both insulators. The front shell member 610d and the rear shell member 610b form an enclosed casing when they are coupled together. In this case, the conductive panel 610c provides the exposed surface and is provided on the side of the front shell member 610d away from the rear shell member 610b. Moreover, the capsule 620 is disposed within the enclosed casing and sealingly attached to the front shell member 610d. In addition, the barrier sheet 632 and the conductive panel 610c are integrally formed, with the overflow aperture 612 being provided in the front shell member 610d. Additionally, a weakened feature, optionally implemented as a groove, may be provided on the conductive panel 610c. The barrier sheet 632 may be torn open along the groove. In more particularity, FIG. 15 schematically shows the barrier sheet 632 that has not been torn open yet, and FIG. 16 schematically shows the barrier sheet 632 that has been torn open. In other embodiments, the weakened feature may be implemented otherwise. The weakened feature is able to withstand a maximum pressure lower than a maximum pressure that the rest of the conductive panel is able to withstand in order to enable the barrier sheet 632 to be broken open at the weakened feature when pulled. Further, the threaded boss 633 is provided on the side of the conductive panel 610c facing the front shell member 610d and may extend into the capsule 620 in order to be more easily coupled to the fastening screw 631.

In practical operation, when the host 400 determines that the patient is in need of defibrillation, the electrode plate 600 is inflated. As a gas pressure therein increases, the hermetic shell 610 will gradually expands, thus enlarging the distance between the defibrillation panel 610a and the rear shell member 610b. As a result, the fastening screw 631 is subjected to a pulling force and causes the threaded boss 633 to pull the barrier sheet 632. When the pulling force increases to a certain level, the barrier sheet 632 will be torn open along the groove, thereby opening the overflow aperture 612. Subsequently, the conductive paste S is squeezed out under the action of the gas pressure and flows through the overflow aperture 612 into a gap between the defibrillation panel 610a and the patient's skin to effectuate an impedance drop.

Figure 19:
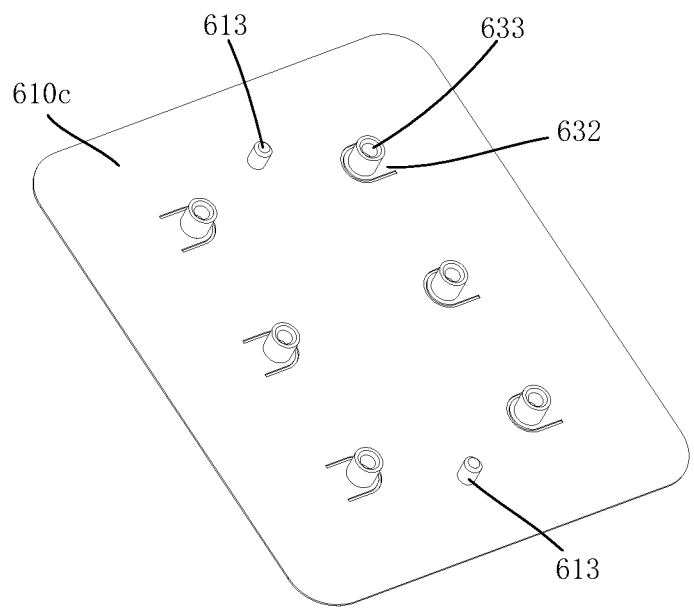
FIG. 19 is a three-dimensional diagram of a conductive panel according to the second embodiment of the present invention.

Preferably, the conductive panel 610 is implemented as a metal plate, the front shell member 610d as a plastic component and the rear shell member 610b as a rubber component. As shown in FIG. 19, the conductive panel 610c may be provided thereon with two terminal posts 613, which are connected by external lead cables to the host 400 to enable delivery of an electric current to the conductive panel 610c. The conductive panel 610c may be glued to the front shell member 610d.

Figure 20:
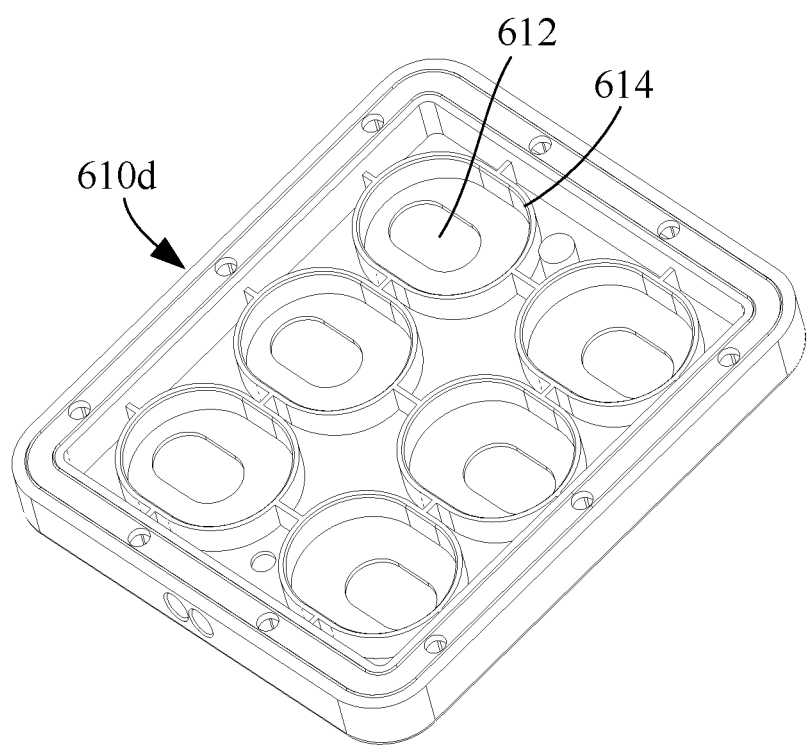
FIG. 20 is a three-dimensional diagram of a front shell member according to the second embodiment of the present invention.

Referring to FIG. 17, the overflow aperture 612 is provided on the front shell member 610d so as to extend therethrough. The conductive panel 610c is attached to the front shell member 610d in such a manner that the barrier sheet 623 exactly covers and closes the overflow aperture 612. Without wishing to be limiting, the overflow aperture 612 may have an oblong shape. Referring to FIG. 20, a capsule receptacle 614 is preferably provided on the side of the front shell member 610d away from the conductive panel 610c. The capsule receptacle 614 is disposed to surround the overflow aperture 612 and has a shape matching that of the capsule 120. In this way, a larger adhesive bonding area can be obtained, ensuring secure attachment of the capsule 620. Referring to FIG. 18, the capsule 620 is made of the same material as is used in the first embodiment. Preferably, the capsule 620 is provided with annular corrugations (not labeled), which enables the capsule 620 to deform by an increased amount when pulled, thus avoiding it from being damaged.

Referring back to FIG. 17, the rear shell member 610b is an insulator optionally made of a metallic or non-metallic material that can deform when the pad is inflated. The rear shell member 610b is optionally made of insulating rubber, PVC or TPU, which is pliable and easily deformable and can enhance wearing comfort. Further, in order to control an amount of deformation of the rear shell member 610b, an inner surface of the rear shell member 610b is preferably provided thereon with a bump 615 protruding toward the front shell member 610d, or annular corrugations, or both.

The hermetic shell 610 is preferred to further include a securing plate 640 disposed on the side of the rear shell member 610b away from the front shell member 610d. The securing plate 640 is configured to secure the rear shell member 610b to the front shell member 610d so that the front shell member 610d and the rear shell member 610b are coupled together to form an enclosed casing. In this embodiment, the securing plate 640, the rear shell member 610b and the front shell member 610d are fastened together with screws. The hermetic shell 610 is preferred to further include a reinforcing plate 650 disposed on the side of the rear shell member 610b away from the front shell member 610d. The reinforcing plate 650 is configured to be coupled to the rear shell member 610b to provide it with support. In this embodiment, the reinforcing plate 650 is provided therein with a through hole. Moreover, part of the fastening screw 631 is received in the through hole in the reinforcing plate 650, the rest is passed successively through a through hole in the rear shell member 610b and the capsule 620, then the rest is threadedly tightened in the threaded boss 633. The inner surface of the rear shell member 610b may be further provided thereon with a protrusion implemented preferably as a flat gasket 660, which is configured to compress and hold the capsule 620 to prevent it from falling off. The securing plate 640, the reinforcing plate 650 and the flat gasket 660 may be formed of a metallic material or non-metallic material, without limiting the present invention in any way.

It is to be understood that the features of this embodiment that are same as those of the first embodiment, such as the cable port, inflation port, exposed surface and number of capsules, are not again described in detail. For details of these features, reference can be made to the disclosure in connection with the first embodiment.

In summary, in the electrode plate and WCD device of the present invention, the force applying component pulls the sealing component off the overflow aperture and thus separates it from the sealing component, under the action of expansion of the hermetic shell, thereby opening the overflow aperture and the outlet orifice of the capsule. In this way, automated application of the conductive paste is achieved, facilitating timely protection of the patient. Compared with breaking the capsule under the action of a sufficiently high gas pressure brutally created by explosion of a gas-producing agent, according to the present invention, by introducing a gas into the electrode plate through the inflation port, it can be ensured that the force applying component pulls the sealing component to cause its complete or partial separation from the overflow aperture under the effect of a relatively safe inflation pressure. Therefore, the electrode plate and WCD device of the present invention provides particularly high safety and reliability. In particular, the electrode plate of the present invention is soft and comfortable, providing the patient with increased wearing comfort and compliance. Additionally, the electrode plate of the present invention is an inexpensive, low-cost disposable product. Apart from these, the electrode plate of the present invention can directly serve as an airbag, dispensing with the need for a separate airbag. This entails a simpler structure and increased ease of operation. Further, in case of multiple capsules being used, an increased amount of released conductive paste, a larger coated area and higher defibrillation safety can be achieved. In particular, during release of the conductive paste, as the cavities of the capsules are isolated from the hollow internal space of the hermetic shell, even when any overflow aperture is opened, no press drop that may make the remaining capsules impossible to be opened anymore will occur within the hermetic shell, ensuring reliable release of the conductive paste.

It is to be understood that features of the present invention have been disclosed in the foregoing preferred embodiments to provide a better understanding of the invention to those skilled in the art. It would be appreciated by those skilled in the art that, on the basis of the disclosure herein, it would be easy to modify the present invention while still achieving the same objects and/or advantages as the embodiments disclosed herein. Those skilled in the art would also recognize that such similar configurations do not depart from the scope of disclosure of this invention and could be subject to various changes, substitutions, and alterations without departing the scope of disclosure of the invention.

What is claimed is:

1. An electrode plate for use in cardiac defibrillation, the electrode plate comprising:
    a hermetic shell having an inflation port and an overflow aperture, the overflow aperture provided in an exposed surface of the hermetic shell, wherein the exposed surface has electrical conductivity;
    a capsule disposed in the hermetic shell, the capsule defining a cavity for storage of a conductive paste therein, the cavity defining an inlet orifice and an outlet orifice, the overflow aperture disposed at the outlet orifice, the cavity isolated from a hollow internal space of the hermetic shell; and
    a sealing structure comprising a sealing component and a force applying component, the sealing component disposed at the overflow aperture, the sealing component configured to close the overflow aperture and the outlet orifice when the hermetic shell is not inflated, the force applying component disposed on the hermetic shell and connected to the sealing component after being inserted into the capsule through the inlet orifice, the force applying component configured to pull the sealing component when the hermetic shell is inflated and expanded, so that the overflow aperture and the outlet orifice are opened and communicated with each other.

2. The electrode plate according to claim 1, wherein part of the force applying component is disposed out of the hermetic shell and the rest of the force applying component is inserted into the capsule through the inlet orifice and threadedly connected to the sealing component.

3. The electrode plate according to claim 2, wherein the overflow aperture is an internally threaded bore, the sealing component is inserted into the internally threaded bore and threadedly connected to the hermetic shell in a sealing manner.

4. The electrode plate according to claim 3, wherein an inner wall of the hermetic shell is provided with a threaded boss providing the internally threaded bore, wherein the threaded boss extends through the outlet orifice into the interior of the capsule, and wherein the capsule is connected to the threaded boss in a sealing manner.

5. The electrode plate according to claim 2, wherein the sealing component comprises a barrier sheet and a connecting member provided on the barrier sheet, the barrier sheet provided on the hermetic shell so as to cover the overflow aperture, wherein the rest of the force applying component is inserted through the inlet orifice into the interior of the capsule and connected to the connecting member.

6. The electrode plate according to claim 5, wherein the connecting member is a threaded boss extending through the outlet orifice into the interior of the capsule and defining a blind threaded bore, wherein the rest of the force applying component is inserted through the inlet orifice into the interior of the capsule and threadedly connected to the threaded boss in a sealing manner.

7. The electrode plate according to claim 1, wherein the hermetic shell comprises a defibrillation panel and a rear shell member, which are coupled together to form an enclosed casing, the defibrillation panel providing the exposed surface, the defibrillation panel having material strength that is higher than material strength of the rear shell member, the rear shell member configured to be deformable as a result of filling a gas into the hermetic shell through the inflation port.

8. The electrode plate according to claim 7, wherein the defibrillation panel comprises a conductive panel and a front shell member, wherein both the front shell member and the rear shell member are insulators, and the conductive panel is a conductor, wherein the front shell member and the rear shell member are coupled together to form the enclosed casing, wherein the conductive panel provides the exposed surface and is disposed on the side of the front shell member away from the rear shell member, wherein the capsule is disposed within the enclosed casing and is disposed on the front shell member, and wherein material strength of the front shell member is higher than the material strength of the rear shell member.

9. The electrode plate according to claim 8, wherein the overflow aperture is disposed in the front shell member, the sealing component is disposed on the conductive panel so as to cover the overflow aperture.

10. The electrode plate according to claim 7, wherein an inner surface of the rear shell member is provided thereon with a bump protruding toward the defibrillation panel and/or annular corrugations.

11. The electrode plate according to claim 7, wherein an inner surface of the rear shell member is provided thereon with a protrusion configured for abutment of the capsule thereagainst.

12. The electrode plate according to claim 1, wherein the capsule comprises a body that defines the cavity and a collar extending outward from the body, the collar defining a hollow channel acting as the outlet orifice, the collar provided with a footing support which extends outward, extends around an axis of the collar and is provided on an inner wall of the hermetic shell, thus securing the capsule.

13. The electrode plate according to claim 1, wherein the sealing component and the overflow aperture are configured so that when a pulling force acting on the sealing component increases to a predetermined value, the sealing component is able to be separated from the overflow aperture, allowing the conductive paste stored in the cavity to flow out of the outlet orifice and flow through the overflow aperture onto the exposed surface.

14. A wearable defibrillation device, comprising a vest, and provided on the vest, a sensing electrode, a host and an airbag, the wearable defibrillation device further comprising the electrode plate as defined in claim 1, which is provided on the vest.

15. The wearable defibrillation device according to claim 14, wherein the electrode plate is configured as the airbag.

* * * * *